United States Patent [19]

Goe et al.

[11] Patent Number: 5,252,741
[45] Date of Patent: Oct. 12, 1993

[54] PROCESSES FOR THE SYNTHESIS OF IMINES, ALDEHYDES, AND UNSYMMETRICAL SECONDARY AMINES

[75] Inventors: Gerald L. Goe, Greenwood; James G. Keay, Indianapolis; Eric F. V. Scriven, Greenwood, all of Ind.; Michael L. Prunier, Vernon, Ill.; Steven J. Quimby, Carmel, Ind.

[73] Assignee: Reilly Industries, Inc., Indianapolis, Ind.

[21] Appl. No.: 871,084

[22] Filed: Apr. 20, 1992

Related U.S. Application Data

[63] Continuation of Ser. No. 565,956, Aug. 10, 1990, abandoned.

[51] Int. Cl.$^5$ .......................................... C07D 213/24
[52] U.S. Cl. .................................. 546/329; 546/315
[58] Field of Search .............. 564/271, 291, 442, 275; 546/329, 225, 340, 286, 315

[56] References Cited

U.S. PATENT DOCUMENTS 2,798,077 7/1957 Schläpfer et al. .................. 546/329

OTHER PUBLICATIONS

Rylander et al., Eng. Tech. Bull., 11, 19 (1970).

*Primary Examiner*—Allen J. Robinson
*Assistant Examiner*—Shailendra Kumar
*Attorney, Agent, or Firm*—Woodard, Emhardt, Naughton Moriarty & McNett

[57] ABSTRACT

Imines are synthesized by the hydrogenation of pyridinecarbonitriles with amines in the presence of a rhodium-loaded catalyst. The resulting imines are stable and may be transiminated and then hydrogenated to form selected secondary amine products or may be hydrolyzed to aldehydes.

Further, a very useful class of unsymmetrical secondary amines represented by the formula $RCH_2NHAr$ (in which R is not aliphatic and Ar is aromatic and not attached to R), which has heretofore been accessible only with some difficulty, can be synthesized by processes herein disclosed utilizing the reductive intermolecular coupling of nitriles and primary aromatic amines.

12 Claims, No Drawings

PROCESSES FOR THE SYNTHESIS OF IMINES, ALDEHYDES, AND UNSYMMETRICAL SECONDARY AMINES

REFERENCE TO RELATED APPLICATION

This application is a continuation of U.S. patent application Ser. No. 07/565,956, filed Aug. 10, 1990, now abandoned.

BACKGROUND OF THE INVENTION

The present invention relates generally to the synthesis of imine intermediates which are useful in preparing aldehydes and unsymmetrical secondary amines, and also to the synthesis of unsymmetrical secondary amines. Specifically, the present invention relates to the preparation of stable imines by hydrogenating a mixture of a pyridinecarbonitrile and a primary amine in the presence of hydrogen and a rhodium-loaded hydrogenation catalyst, and the subsequent use of these imines as precursors of aldehydes and secondary amines. Further, the present invention specifically relates to the preparation of unsymmetrical secondary amines of the general formula $RCH_2NHAr$, wherein R is non-aliphatic and Ar is aromatic, by reductively coupling a nitrile of the formula RCN and a primary aromatic amine.

Although the presence of imine intermediates in nitrile hydrogenations has been proposed and imines are suspected by-products from the hydrogenation of nitriles in the presence of primary amines, commercially useful quantities of selected imine products, as well as isolation or characterization of the same, from the hydrogenation of a pyridinecarbonitrile and a primary amine has been unknown. Rylander, P. N. and Hasbrouck, L., *Eng. Tech. Bull.*, 11, 19 (1970), identified (by infrared) small quantities of uncharacterized imine as some unspecified portion of the miscellaneous compounds formed upon hydrogenation of benzonitrile and butylamine to produce high yields of various amines. No miscellaneous compounds were reported when a rhodium catalyst was used. Moreover, the Rylander and Hasbrouck work suggests that amine products are nearly quantitatively favored when nitrile hydrogenations take place in the presence of amines. In contrast, Applicants have discovered that pyridinecarbonitriles hydrogenated in the presence of rhodium and a primary amine unexpectedly form imines in good yield.

Imines have also been proposed as intermediates to explain the alkyl group exchange reactions of amines. Murahashi, S., et al., *J. Am. Chem. Soc.*, 105, 5002 (1983).

Among other things, imines made according to Applicants' invention are beneficial intermediates and precursors. For instance, certain free aldehydes are known to be unstable and reactive. By way of illustration, 3-pyridinecarboxaldehyde oxidizes to give the solid carboxylic acid, i.e., niacin, upon exposure to ambient conditions. The solidification indicates a chemical change which makes the substance useless to its intended purpose. As a consequence, aldehydes of this sort are difficult to handle. Often referred to as masked aldehydes, imines can be hydrolyzed through nucleophilic attack to the corresponding aldehyde. This property of imines makes them ideal aldehyde precursors which may be stored until the aldehyde is needed. At that time, the imine is hydrolyzed to form the aldehyde. However, this same property has in the past caused some difficulties in imine synthesis. Under synthesis conditions, the imine may tend to hydrolyze to the aldehyde so that relatively little imine product is obtained.

Applicants have also discovered that yields of desired unsymmetrical secondary amines from nitrile hydrogenations are unexpectedly improved appreciably when stable imine intermediates are used according to the present invention. Nitrile hydrogenations are known to result in the production of symmetrical secondary amines. Schwoegler, E. J. and Adkins, H., *J. Am. Chem. Soc.*, 61, 3499 (1939) taught that the ratio of primary to secondary amines in nitrile hydrogenations is seldom greater than 3 to 1. These researchers also taught that the yield of primary amine can be increased through addition of ammonia. When amines are added to the nitrile hydrogenation mixture, mixed secorndary amines are produced in various amounts since the partially hydrogenated nitrile and the added amine compete to combine into secondary products. Accordingly, the mixed secondary amines which form detract from the yield of desired unsymmetrical product. The effect of this decrease in yield is especially great when the reactants are expensive.

Applicants' invention overcomes the problem of interfering mixed secondary amine by-products in the synthesis of unsymmetrical secondary amines. An intermediate imine made according to Applicants' process can be isolated and then manipulated using transimination techniques to displace one group of the imine with a more preferred group. The resulting imine may then be further hydrogenated to yield the selected unsymmetrical secondary amine in surprisingly good yield. Applicants are unaware of any reported reaction processes for the production of unsymmetrical secondary amines utilizing stable imine intermediates and subjecting such intermediates to transimination prior to final hydrogenation.

In addition to the selectivity with which unsymmetrical amine products can be made, enhanced efficiency and cost effectiveness are possible. In the typically less quantitative imine synthesis step of the reaction, a cheaper or more abundant or available primary amine reactant may be used to react with the nitrile. The amine used for the transimination step might then be more costly, less readily available, etc. Valuable resources are consequently conserved.

Another aspect of Applicants' invention is the discovery that a very useful class of unsymmetrical secondary amines represented by the formula $RCH_2NHAr$ (in which Ar is not attached to R) can be synthesized by the processes herein disclosed that utilize the reductive intermolecular coupling of non-aliphatic nitriles and primary aromatic amines. This class of unsymmetrical secondary amines has heretofore been accessible only with some difficulty.

Secondary amines of the general formula $RCH_2NHAr$, as well as imines of the general formula $RCH=NHAr$, are known to be useful, for example, in the synthesis of agricultural chemicals, such as the fungicides described in U.S. Pat. No. 4,358,446, "Use as Fungicides of N-(3-Pyridylmethyl)-N-acyl Anilines," issued to Ten Haken et al. in 1982. Ten Haken et al. teach that imines can be produced by coupling carbonyl pyridine compounds and amines with the loss of water.

The reductive intermolecular coupling of nitriles and primary aliphatic amines in molar ratios of about 1:1 is generally known to give unsymmetrical secondary amines, according to the following general reaction:

$$RCN + R'NH_2 + H_2 \rightarrow RCH_2NHR' + RCH_2NH_2.$$

These reductive couplings are known to take place between certain classes of nitriles and certain classes of amines. Applicants are unaware, however, of any instance where non-aliphatic nitriles have been reported to reductively couple with aromatic amines forming an unsymmetrical secondary amine product.

For example, in U.S. Pat. No. 2,798,077, "Preparation of Methyl-(beta-picolyl)-Amine," issued to R. Schlapfer et al. in 1957, it is disclosed that 3-cyanopyridine can be hydrogenated in the presence of excess methylamine and a Raney nickel catalyst to yield N-methyl-3-picolylamine and beta-picolylamine. Separation of the beta-picolylamine is then required.

Aromatic amines that also contain nitrile groups have been reported to cyclize during intramolecular nitrile reduction to synthesize bicyclic systems, such as indoles. Rylander, P. N., *Catalytic Hydrogenation Over Platinum Metals*, p.215 (Academic Press, 1967).

Kindler, K. and Hesse, F., *Arch. Pharm.*, 271, 439 (1933) disclosed the synthesis of secondary and tertiary amines by the hydrogenation of nitriles. Primary and secondary aliphatic amines were added to the reaction mixture to yield various amine products. An intermediate aldime was proposed to explain the variety of products obtained.

Aliphatic nitriles have been shown to reductively couple with aromatic and aliphatic amines. U.S. Pat. No. 3,209,029 issued to Abramo et al. in 1965 discloses the synthesis of aminoalkyl-aromatic-ethylamines by the reduction of cyano-alkyl-aromatic-acetonitriles in the presence of a primary amine.

Further, certain catalysts are known to favor certain amine products in the hydrogenation of nitriles. In the hydrogenation of basic nitriles, including 3-cyanopyridine, to primary amines, formation of secondary symmetrical amine has been prevented by the use of a Raney nickel catalyst and the presence of ammonia. Various other catalysts including palladium and platinum catalysts, were reported to favor the formation of secondary amines. Huber, W., *J. Am. Chem. Soc.*, 66, 876 (1944).

Rylander and Hasbrouck have discussed catalyst selectivity for certain amine products in the reductive coupling of benzonitrile and of aliphatic nitriles in the presence of aliphatic amines. Rhodium on carbon, palladium on carbon and platinum on carbon were investigated for amine selectivity. Palladium was generally found to be a poor catalyst for reductive couplings to form amines, while rhodium and platinum were selective for certain secondary amines.

The reductive intermolecular coupling of aromatic or heteroaromatic nitriles and aromatic primary amines to yield unsymmetrical secondary amines has, however, remained unknown. In fact, Juday and Adkins reported that aniline did not couple with nitriles under conditions that were effective for coupling aliphatic amines with nitriles. Juday, R. E. and Adkins, H., *J. Am. Chem. Soc.*, 77, 4559 (19⁝⁝). In other work, Juday reported that no mixed secondary amine product formed from the addition of prim⁀ ⁀y amines to the hydrogenation mixture of aromatic nitriles. The yield of tetrahydrohydrobenzamide did, however, increase. Juday, R. E., *Proc. Montana Acad. Sci.*, 7-8, 84 (1947-48).

SUMMARY OF THE INVENTION

Accordingly, Applicants have discovered a process for preparing a very useful class of imine compositions through the step of hydrogenating a mixture of a 3-cyanopyridine and a primary amine in the presence of a rhodium-loaded hydrogenation catalyst.

Applicants' have also discovered that yields of desired unsymmetrical secondary amines can be improved appreciably by first synthesizing an imine intermediate and then manipulating the imine intermediate to the desired amine. This preferred aspect of Applicants' discovery includes a process for preparing an unsymmetrical secondary amine composition, e.g., of the formula $RCH_2NHR^2$ where R is a 3-pyridyl group, by hydrogenating a mixture of 3-cyanopyridine and a first primary amine, e.g., of the formula $R'NH2$, in the presence of a rhodium-loaded hydrogenation catalyst to yield a first stable imine intermediate, e.g., having the formula $RCH=NR'$, transiminating the resulting stable imine intermediate with a second primary amine, e.g., having the formula $R^2NH_2$, to yield a second stable imine intermediate, e.g., having the formula $RCH=NR^2$ and then hydrogenating the second stable imine intermediate to thereby form the unsymmetrical secondary amine composition.

A still further embodiment of Applicants' discovery involves the preparation of an aldehyde from a stable imine precursor made according to the present process. The aldehydes are prepared by hydrogenating a mixture of a 3-cyanopyridine and a primary amine in the presence of a rhodium-loaded hydrogenation catalyst to form a stable imine intermediate, separating the hydrogenation catalyst from the imine intermediate and hydrolyzing the imine intermediate to the corresponding aldehyde.

In another aspect of the present invention, Applicants have discovered that a very useful class of unsymmetrical secondary amines represented by the formula $RCH_2NHAr$ (in which R is non-aliphatic and Ar is aromatic), which have heretofore been accessible only with some difficulty, can be synthesized by processes disclosed herein. These processes include the preparation of an unsymmetrical amine composition of the formula $RCH_2NHAr$, where R is not aliphatic, and Ar is aromatic, by intermolecularly coupling a nitrile of the formula RCN and a primary aromatic amine of the formula $ArNH_2$ in the presence of hydrogen and a hydrogenation catalyst.

Additional objects and advantages of the present invention will be apparent from the following description.

DESCRIPTION OF THE PREFERRED EMBODIMENTS

A first embodiment of the present invention is a process for preparing stable imine compositions by hydrogenating a mixture of a cyanopyridine and a primary amine in the presence of a rhodium-loaded catalyst according to the following general reaction:

$$2RCN + 2R'NH_2 + H_2 \rightarrow 2RCH=NR' + NH_3$$

According to Applicants' discovery, when rhodium is used as the hydrogenation catalyst the above reductive intermolecular coupling reaction can be stopped and a stable $RCH=NR'$ intermediate obtained and isolated. Suitable rhodium-loaded catalysts include rhodium on carbon, rhodium on alumina and other rhodium containing catalysts. The rhodium loading may be as is convenient, but is preferably about 5% by weight. The amount of catalyst relative to the starting materials, can be chosen to give a convenient rate of reaction. To date Applicants have used between about 5% and about 38% by weight of the catalyst relative to the nitrile starting material present. If so desired, the rhodium catalyst may be separated and recovered for later use using known recovery methods. In fact, rhodium on carbon has been recycled in the reductive coupling of 3-cyanopyridine with n-butylamine several times without a perceivable loss in catalytic activity.

A number of cyanopyridine and primary amine combinations may be used in this aspect of the present invention. At present, 3-cyanopyridine is the preferred nitrile. The amine may be nearly any primary amine. Examples of suitable amines are anilines and substituted anilines, n-butylamine and p-toluidine. The molar amount of primary amine present in the reaction mixture relative to the molar amount of nitrile is preferably at least about 1:1, although other molar ratios may prove advantageous. In the case where the imine is intended for use as a precursor or intermediate, the amine is preferably one which is relatively inexpensive, n-butylamine, for example. Further, if the amine used is a low-boiling one, then it may be boiled off to recover the imine product. Still further, the excess amine may be condensed and recovered for later use.

The pressures and temperatures used in the preferred process of this embodiment can be chosen for convenience and practicality, and can be thereby optimized in the usual fashion by those ordinarily skilled in this area. For example, hydrogen pressures ranging from about 50 to about 500 psig have been effectively used. The preferred pressure from testing thus far is about 50 psig. Similarly, temperatures ranging from about 20° to about 100° C. have been used and proven suitable. The preferred temperature to date is one somewhat elevated above ambient, although this is not required.

If so desired, the reaction progress may be monitored by the pressure drop. After about one equivalent of hydrogen has been used, the reaction is preferably stopped by methods readily apparent to those skilled in the art. These methods include, but are not limited to, releasing the pressure and thus the hydrogen charge, lowering the temperature and/or removing the hydrogenation catalyst.

Isolation of the imine product may be by ordinary techniques, including recrystallization and distillation. The product might then be stored for later use as a reactant, end-product, precursor, etc. Such later uses include use in two other embodiments of the present invention, described below. When intended as an aldehyde precursor, according to the third embodiment below, it is often preferable to isolate the stable imine for storage until the aldehyde is needed. This is so since the imine (or masked aldehyde) is often appreciably more stable than the corresponding aldehyde and can be stored for appreciably longer times without significant degradation.

The above embodiment is useful for the synthesis of imines of general application as intermediates, precursors or end-products. As noted, Applicants have found the imine intermediate to be superior for the production of aldehydes and unsymmetrical secondary amines. Thus, a second embodiment of Applicants' invention concerns the synthesis of unsymmetrical secondary amines by first synthesizing an amine precursor according to the first embodiment. The imine precursor may then be manipulated to the desired amine. Transimination is included in the preferred manipulation technique. This reaction sequence results in unexpectedly improved yields of the desired amine, with corresponding decreases in undesired mixed side products.

As discussed, by-products, such as symmetrical secondary amines, detract from the yield of the desired unsymmetrical secondary amine. The yield loss to such by-products might be serious, depending on the relative electronic effects of the R and R' groups. In the second embodiment of the present invention, usable product can be recovered from what were previously undesirable symmetrical by-products by combining reductive intermolecular coupling of nitriles and amines with transmission (also known as metathesis) techniques to synthesize the desired unsymmetrical secondary amines. In so doing, it has also been discovered that N-(2,4-difluorophenyl)-3-picolylamine, and other N-substituted 3-picolylamines that were not heretofore as easily prepared in acceptable yields by the direct reductive intermolecular coupling of the appropriate nitriles and primary aromatic amines, can be prepared in greatly increased yields.

In general, the initial step of the reaction sequence forms an imine of the general formula $RCH=NR'$. Using the concept of transimination, the stable imine intermediary may be manipulated with a second primary amine, $R^2NH_2$ to form a second stable intermediary $RCH=NR^2$ and $R'NH_2$. The $R'NH_2$ might then be removed by distillation or acidification and extraction, and recovered, thereby enriching the reaction mixture in the desired second imine. The reaction mixture, enriched in the exemplary stable intermediary precursor $RCH=NR^2$, can then be further hydrogenated to reduce the precursor to the unsymmetrical secondary amine $RCH_2NHR^2$. This entire exemplary reaction process may be represented in three substeps, as follows:

$$RCN + R'NH_2 + H_2 \rightarrow RCH=NR' \quad (a)$$

$$RCH=NR' + R^2NH_2 \rightarrow RCH=NR^2 + R'NH_2 \quad (b)$$

$$RCH=NR^2 + H_2 \rightarrow RCH_2NHR^2 \quad (c)$$

wherein R is non-aliphatic, R' may be aliphatic or non-aliphatic, and $R^2$ may be aromatic but is not attached to R or R'.

Substep (a) proceeds according to the first embodiment of Applicants' invention. If desired or necessary, the intermediate $RCH=NR'$ (or the intermediate $RCH=NR^2$) can be isolated by the usual techniques of distillation or recrystallation, but this is not required.

Substep (b), the transimination step, will proceed under the influence of electronic effects to completion. If the $R'NH_2$ amine has a suitably low boiling point (preferably lower than that of the solvent utilized, if any, but at least lower than that of the second amine $R^2NH_2$), it may be driven from the reaction solution by heating, leaving the preferred intermediate, $RCH=NR^2$, in the reaction mixture. Another method of driving the second substep to the desired degree of completion is to rely on the differences in basicity of aliphatic and aromatic amines. This method has the most application when the first primary amine is aliphatic and the second is aromatic. Adding acid to the mixture of the RCH=NR' intermediary, and the aromatic amine, ArNH$_2$, generates the anil, RCH=NAr, and the more basic R'NH$_2$ as an acid salt. This equilibrium has been demonstrated by Singh et al., *J. Chem. Soc. Perkin I*, 2091 (1986). Further, concentrated HCL or another acid may be added to promote the transimination.

An additional aspect of the second embodiment is Applicants' discovery that the initial hydrogenation reaction (a) can be enhanced appreciably if an aliphatic amine, R'NH$_2$, is utilized. Then the manipulation of the RCH=NR' intermediary with transimination techniques and a second primary amine R$^2$NH$_2$ results in greatly improved yields of the amine precursor RCH=NR$^2$, and thus the unsymmetrical secondary amine products. The advantages of utilizing an aliphatic amine in substep (a) include: (1) aliphatic amines are effectively coupled in a lower molar ratio to the nitrile (1:1) than, for example, aromatic amines such as 2,4-difluoroaniline or other amines with pKa's lower than R'NH$_2$; (2) aliphatic amines are generally cheaper starting materials; (3) overall yields are improved because of the greater yields achievable in the first hydrogenation, (4) the kinetics of the first hydrogenation are improved with aliphatic amines versus aromatic amines; (5) many different unsymmetrical secondary amines can be prepared from the same initial intermediate RCH=NR' by transimination with various second primary amines, while non-aliphatic groups might be harder to displace; (6) amines with functional groups that would not survive initial reduction, such as —CHO and —CN, can be substituted in the transimination step (if they would survive the conditions of that step); and (7) costly primary aromatic amines can be utilized more efficiently in the transimination step rather than the initial hydrogenation step.

In any event, practically any amine R'NH$_2$ can be used in substep (a). Preferred primary amines to date have been aliphatic amines such as n-butylamine, t-butylamine and cyclohexylamine, with n-butylamine being particularly preferred since it is cheap and low boiling. In the initial hydrogenation step, aliphatic amines are preferably present in about a molar ratio of 1:1 relative to the nitrile. On the other hand, aromatic amines are preferably present in excess of about 1:1. The transimination step (b) typically requires about a 1:1 molar ratio of imine to second primary amine almost regardless of the second amine's character.

The catalyst for the third substep, or final hydrogenation, may be any suitable hydrogenation catalyst. Such catalysts are commonly precious metal catalysts although others may be suitable. Preferred catalysts to date include palladium, platinum and rhodium containing catalysts.

Moreover, the reaction conditions may be those which are typically used in imine hydrogenations, including elevated pressure from the hydrogen charge and elevated temperature. Of course, the conditions may be optimized depending upon the desired reaction rate, etc.

In yet a third embodiment of Applicants' invention, the imine precursor (or masked aldehyde) made according to the first embodiment of the invention is hydrolyzed to an aldehyde. Imines are known aldehyde precursors. Imines are however, more stable than aldehydes and, consequently, make a desirable storage medium. When it becomes time to use the aldehyde, the imine is simply hydrolyzed in the presence of a base. Particularly advantageous uses of the present invention are described in Examples 5 and 6. In these Examples, N-butyl-3-pyridylmethyleneimine is hydrolyzed to 3-pyridinecarboxaldehyde, a particularly noxious, although useful, aldehyde. Example 5 illustrates a base hydrolysis, while Example 6 is an acid hydrolysis.

A fourth embodiment of the present invention is the surprising discovery that nitriles hydrogenated in the presence of primary aromatic amines yield reasonable amounts of unsymmetrical secondary amines of the general formula RCH$_2$NHAr. This reaction can be expressed generally as follows:

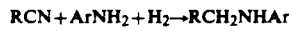

$$RCN + ArNH_2 + H_2 \rightarrow RCH_2NHAr$$

wherein R is not aliphatic, and Ar is aromatic.

As an example, Applicants have discovered that N-(2,4-difluorophenyl)-3-pyridylmethylamine is unexpectedly successfully prepared in yields heretofore unknown in the reductive coupling of 3-cyanopyridine with 2,4-difluoroaniline. However, Applicants contemplate that other nitriles may come within the scope of the invention. Preferred nitriles in work done to date include pyridinecarbonitriles.

Also within the scope of this embodiment are a large number of primary aromatic amines, including unsubstituted aniline and substituted anilines, particularly those that contain halogen or alkyl substituents, or both. Preferred primary aromatic amines to date have been polyhaloanilines, and particularly preferred have been polyfluoroanilines, such as 2,4-difluoroaniline.

The catalyst for the hydrogenation of nitriles and aromatic amines can be chosen among the so-called precious metal catalysts. Preferred catalysts to date include platinum on carbon; palladium supported on carbon or barium sulfate; and rhodium on carbon, which has resulted in much higher conversion than either palladium or platinum and with acceptable selectivity. The metal loading can be as convenient, but the preferred level in Applicants' work to date has been about 5% by weight. The amount of catalyst utilized, relative to the amount of starting materials, can be chosen to give a convenient rate of reaction. Applicants have used to date between about 5 and about 38% by weight of catalyst relative to the amount of the nitrile starting material.

Pressures and temperatures for the disclosed process can be chosen for convenience, and can be optimized in the usual fashion. To date, Applicants have preferred to use a hydrogen pressure ranging from about 50 to about 500 psig, and a temperature ranging from about 20 to about 100 deg C., with about ambient temperature and a hydrogen pressure of about 50 psig being most preferred.

The amount of primary aromatic amine relative to the amount of nitrile starting material, should be in the molar ratio of at least about 1:1 for amines with high pKa's, such as aniline. In work done to date, amines with low pKa's have required molar ratios of 3:1 to 7:1 (amine:nitrile) to maintain acceptable selectivity. For example, molar ratios of 3:1 2,4-difluoroaniline to 3-cyanopyridine have been required to yield acceptable results. Higher ratios can be also used, up to and including the use of the amine as the solvent. Under these conditions, known side reactions, including the formation of primary and secondary amines RCH$_2$NH$_2$ and (RCH$_2$)$_2$NH, are lessened by mass-action effects. In general, most of the amine can be recovered for reuse.

However, the solvent utilized for the present invention is largely a matter of choice. Polar protic solvents are generally preferred. In their work to date, Applicants have used hexane, methanol, ethanol and isopropanol as solvents. The preferred solvent to date has been methanol because of the high solubility of the starting materials and end products in methanol.

For the purpose of promoting a better understanding of the processes of the Applicants' invention, reference will be made in the Examples that follow to specific instances of their use. These Examples are for illustration only, and no limitation of the scope or breadth of the Applicants' invention is thereby intended.

EXAMPLE 1

Preparation of N-(2,4-difluorophenyl)-N-(3-pyridylmethylene)imine

A mixture of 3-cyanopyridine (5.2 g), 2,4-difluoroaniline (96.7 g) and 5% rhodium on carbon (0.5 g) was treated with hydrogen at 60 psig and 30 deg C. in a rocking autoclave for thirteen hours. The catalyst was removed by filtration and the filtrate was analyzed by glc to show 3.6 g of N-(2,4-difluorophenyl)-N-(3-pyridylmethylene)imine.

EXAMPLE 2

Preparation of N-(4-methylphenyl)-N-(3-pyridylmethylene)imine

A mixture of 3-cyanopyridine (20.8 g), 100 mL of methanol, p-toluidine (21.4 g), and 5% rhodium on carbon (1.0 g) was treated with hydrogen at 50 psig and 50 deg C. for eight hours in a rocking autoclave. The catalyst was removed by filtration and the filtrate was analyzed by glc to show 17.7 g of N-(4-methylphenyl)-N-(3-pyridylmethylene)imine,

EXAMPLE 3

Preparation of N-(3-pyridylmethyl)-N-(3-pyridylmethylene)imine, transimination to N-(2,4-difluorophenyl)-N-(3-pyridylmethylene)imine, and reduction to N-(2,4-difluorophenyl)-N-(3-pyridylmethyl)amine (a) A mixture of 3-cyanopyridine (72.8 g), 350 mL of methanol, 2,4-difluoroaniline (270.9 g), and 5% rhodium on carbon (3.5 g) was treated with hydrogen at 50 psig and 30 deg C. for 30 hours. The catalyst was removed by filtration and the filtrate was analyzed by glc to show 30.4 g of N-(2,4-difluorophenyl)-N-(3-pyridylmethylidine)imine, 2.0 g of N-(2,4-difluorophenyl)-N-(3-pyridylmethyl)amine, and 50.2 g of N-(3-pyridylmethyl)-N-(3-pyridylmethylene)imine. The methanol was removed by distillation.

(b) Concentrated hydrochloric acid (60 mL) in distilled water (200 mL) was added to the residue to promote transimination. The organic layer was separated, washed with 50 mL of 10% aqueous sodium hydroxide, and dried over magnesium sulfate.

(c) The resulting material, 350 mL of methanol, and 5% palladium on carbon (5.0 g) were treated with hydrogen at 400 psig and 35 deg C. for two hours in a rocking autoclave. The catalyst was removed by filtration and the solution was distilled to give 59.0 g of N-(2,4-difluorophenyl)-N-(3-pyridylmethyl)amine.

EXAMPLE 4

Preparation of N-(butyl)-N-(3-pyridylmethylene)imine, transimination to N-(2,4-difluorophenyl)-N-(3-pyridylmethylene)imine, and reduction to N-(2,4-difluorophenyl)-N-(3-pyridylmethyl)amine (a) A mixture of 3-cyanopyridine (104.0 g), 500 mL of methanol, n-butylamine (73.0 g), and 5% rhodium on carbon catalyst (10.0 g) was treated with hydrogen at 50 psig and 35 deg C. for seven hours in a rocking autoclave. The catalyst was removed by filtration and the filtrate analyzed by glc to show 99.7 g of N-(n-butyl)-N-(3-pyridylmethylene)imine and 18.2 g of N-(3-pyridylmethyl)-N-(3-pyridylmethylene)imine. Methanol and excess n-butylamine were removed by distillation.

(b) To the resulting concentrate were added methylene chloride (600 mL), water (300 mL), concentrated hydrochloric acid (75 mL), and 2,4-difluoroaniline (117 g). The mixture was stirred for three hours at room temperature. The methylene chloride was separated, washed with 10% aqueous sodium hydroxide, and dried over magnesium sulfate. The solvent was removed by evaporation and the resulting brown solid was dissolved in 450 mL of methanol.

(c) To this was added 5% palladium on carbon catalyst (6.0 g) and the mixture was treated with hydrogen at 400 psig and 32 deg C. for two hours in a rocking autoclave. The catalyst was removed by filtration and the filtrate was distilled to give 21.7 g (30%) of N-(2,4-difluorophenyl)-N-(3-pyridylmethyl)amine.

EXAMPLE 5

Preparation of 3-Pyridinecarboxaldehyde by base hydrolysis

N-butyl-N-(3-pyridylmethylene)imine (18.6 g., 0.1 mol), made according to step (a) of Example 4 above, was heated at reflux in water (100 ml) in the presence of NaOH (0.2 mol). Butylamine was recovered by distillation. The solution was cooled and the product extracted into dichloromethane (3×50 mls). After drying over magnesium sulfate, the combined extracts were distilled and 3-pyridinecarboxaldehyde was obtained as a clear colorless liquid.

EXAMPLE 6

Preparation of 3-Pyridinecarboxaldehyde by acid hydrolysis

N-butyl-N-(3-pyridylmethylene)imine (18.6 g., 0.1 mol), made according to step (a) of Example 4 above, was heated at reflux in water (100 ml) in the presence of HCl (1.1 mol) until no further starting material was detected by thin layer chromatography. After cooling and pH adjustment, the solution was extracted with dichloromethane (3×50 mls). After combination, the organic extracts were distilled and dried. 3-pyridinecarboxaldehyde was distilled at 95–97 degrees C. and 15 mm Hg as a clear colorless liquid.

EXAMPLE 7

Preparation of N-phenyl-N-(3-pyridylmethyl)amine

A mixture of 3-cyanopyridine (10.4 g), aniline (101.8 g) and a 5% rhodium on carbon catalyst (1.0 g) was treated with hydrogen at 60 psig 30 deg C. for 13 hours in a rocking autoclave. The catalyst was removed by filtration and the filtrate analyzed by glc to show 3.7 g of N-phenyl-N-(3-pyridylmethyl)amine.

EXAMPLE 8

Preparation of
N-(2,4-Difluorophenyl)-N-(3-pyridylmethyl)amine

A mixture of 3-cyanopyridine (10.4 g), 2,4-difluoroaniline (129.1 g) and a 5% rhodium on carbon catalyst (1.0 g) was treated with hydrogen at 60 psig and 25-30 deg C. until two equivalents of hydrogen had reacted. The hydrogen pressure was incrementally increased to 400 psig during the course of the reaction. After cooling, venting and purging with nitrogen, the catalyst was removed by filtration. The filtrate analyzed and found to contain 10.4 g of N-(2,4-diflourophenyl)-N-(3-pyridylmethyl)amine which could be isolated by distillation (158-164 deg. C. @ 3mm Hg) and recrystallization (cyclohexane) to give a white solid with a melting point of 88.5-90 deg C.

EXAMPLE 9

Preparation of
N-(4-methylphenyl)-N-(3-pyridylmethyl)amine

A mixture of 3-cyanopyridine (10.4 g), p-toluidine (107.2 g) and a 5% rhodium on carbon catalyst (1.0 g) was treated with hydrogen at 60 psig and 25-30 deg C. until two equivalents of hydrogen had reacted. The hydrogen pressure was incrementally increased to 400 psig during the course of the reaction. After cooling, venting and purging with nitrogen, the catalyst was removed by filtration. The filtrate analyzed and found to contain 12.7 g of N-(4-methylphenyl)-N-(3-pyridylmethyl)amine which could be isolated by distillation (158-164 deg. C. @ 3 mm Hg) and recrystallization (cyclohexane).

What is claimed is:

1. A process for preparing an imine composition comprising the step of:
    hydrogenating a mixture of a 3-cyanopyridine and a primary amine in the presence of a rhodium-loaded hydrogenation catalyst.
2. The process of claim 1 in which the rhodium-loaded catalyst is rhodium on carbon.
3. The process of claim 2 in which the rhodium-loaded catalyst is about 5% rhodium on carbon.
4. The process of claim 1 in which the primary amine is an aromatic amine.
5. The process of claim 1 in which the primary amine is an aliphatic amine.
6. The process of claim 1 and further comprising the steps of separating and recovering the hydrogenation catalyst.
7. A process for preparing an aldehyde comprising the steps of:
    hydrogenating a mixture of a 3-cyanopyridine and a primary amine in the presence of a rhodium-loaded hydrogenation catalyst to form a stable imine intermediate;
    separating the hydrogenation catalyst from the imine intermediate; and
    hydrolyzing the imine intermediate to a corresponding aldehyde.
8. The process of claim 7 in which the rhodium-loaded catalyst is rhodium on carbon.
9. The process of claim 8 in which the rhodium-loaded catalyst is about 5% rhodium on carbon.
10. The process of claim 7 in which the primary amine is an aliphatic amine.
11. The process of claim 10 in which said hydrogenating is in the presence of a solvent.
12. The process of claim 11 in which the solvent is the primary amine.